(12) United States Patent
Balsara et al.

(10) Patent No.: US 8,563,168 B2
(45) Date of Patent: Oct. 22, 2013

(54) HIGH ELASTIC MODULUS POLYMER ELECTROLYTES

(75) Inventors: Nitash Pervez Balsara, El Cerrito, CA (US); Mohit Singh, Berkeley, CA (US); Hany Basam Eitouni, Berkeley, CA (US); Enrique Daniel Gomez, Princeton, NJ (US)

(73) Assignee: The Regents of The University of California, Oakland, CA (US)

( * ) Notice: Subject to any disclaimer, the term of this patent is extended or adjusted under 35 U.S.C. 154(b) by 887 days.

(21) Appl. No.: 12/225,934

(22) PCT Filed: Apr. 3, 2007

(86) PCT No.: PCT/US2007/008435
§ 371 (c)(1),
(2), (4) Date: Jun. 19, 2009

(87) PCT Pub. No.: WO2007/142731
PCT Pub. Date: Dec. 13, 2007

(65) Prior Publication Data
US 2009/0263725 A1    Oct. 22, 2009

Related U.S. Application Data

(60) Provisional application No. 60/744,243, filed on Apr. 4, 2006, provisional application No. 60/820,331, filed on Jul. 25, 2006.

(51) Int. Cl.
*H01M 6/04* (2006.01)
*C08C 19/42* (2006.01)
*H01M 6/00* (2006.01)
*C08C 19/00* (2006.01)

(52) U.S. Cl.
USPC ............. 429/188; 429/207; 525/88; 525/90; 525/92 H; 525/360; 525/366

(58) Field of Classification Search
USPC ............ 429/188, 192, 207; 525/88, 90, 92 H, 525/360, 366
See application file for complete search history.

(56) References Cited

U.S. PATENT DOCUMENTS

| | | | |
|---|---|---|---|
| 3,355,513 A | 11/1967 | Sadron | |
| 3,711,412 A | 1/1973 | Sawyer | |

(Continued)

FOREIGN PATENT DOCUMENTS

| | | |
|---|---|---|
| DE | 297281 | 1/1992 |
| EP | 1 553 117 | 7/2005 |

(Continued)

OTHER PUBLICATIONS

U.S. Appl. No. 12/271,829, "Solid Electrolyte Material Manufacturable by Polymer Processing Methods", Singh et al., filed Nov. 14, 2008.

(Continued)

*Primary Examiner* — Duc Truong
(74) *Attorney, Agent, or Firm* — Weaver Austin Villeneuve & Sampson LLP

(57) ABSTRACT

A polymer that combines high ionic conductivity with the structural properties required for Li electrode stability is useful as a solid phase electrolyte for high energy density, high cycle life batteries that do not suffer from failures due to side reactions and dendrite growth on the Li electrodes, and other potential applications. The polymer electrolyte includes a linear block copolymer having a conductive linear polymer block with a molecular weight of at least 5000 Daltons, a structural linear polymer block with an elastic modulus in excess of $1 \times 10^7$ Pa and an ionic conductivity of at least $1 \times 10^{-5}$ Scm$^{-1}$. The electrolyte is made under dry conditions to achieve the noted characteristics.

37 Claims, 15 Drawing Sheets

(56) References Cited

U.S. PATENT DOCUMENTS

| | | | |
|---|---|---|---|
| 4,311,566 | A | 1/1982 | McCann |
| 4,582,876 | A | 4/1986 | Weemes |
| 4,657,833 | A | 4/1987 | Hadley et al. |
| 5,013,619 | A | 5/1991 | Cook |
| 5,196,484 | A | 3/1993 | Giles |
| 5,219,681 | A | 6/1993 | Yamada et al. |
| 5,523,180 | A | 6/1996 | Armand et al. |
| 5,622,792 | A | 4/1997 | Brochu |
| 5,639,574 | A | 6/1997 | Hubbard |
| 5,658,685 | A | 8/1997 | Oliver |
| 6,096,234 | A | 8/2000 | Nakanishi |
| 6,322,924 | B1 | 11/2001 | Hirahara et al. |
| 6,361,901 | B1 | 3/2002 | Mayes |
| 6,428,933 | B1 | 8/2002 | Christensen et al. |
| 6,537,704 | B1 | 3/2003 | Akashi |
| 6,673,273 | B2 | 1/2004 | Ba Le et al. |
| 6,743,550 | B2 | 6/2004 | Gan |
| 6,749,961 | B1 | 6/2004 | Nguyen et al. |
| 6,835,495 | B2 | 12/2004 | Michot |
| 6,841,601 | B2 | 1/2005 | Serpico et al. |
| 7,026,071 | B2 | 4/2006 | Mayes et al. |
| 7,282,302 | B2 | 10/2007 | Visco |
| 7,315,106 | B2 | 1/2008 | Asaka |
| 7,318,982 | B2 | 1/2008 | Gozdz |
| 8,268,197 | B2 | 9/2012 | Singh et al. |
| 2003/0094599 | A1 | 5/2003 | Le et al. |
| 2004/0151985 | A1 | 8/2004 | Munshi |
| 2005/0034993 | A1 | 2/2005 | Gozdz et al. |
| 2005/0181254 | A1 | 8/2005 | Uensal et al. |
| 2005/0221193 | A1 | 10/2005 | Kinouchi et al. |
| 2005/0256256 | A1 | 11/2005 | Muramoto et al. |
| 2006/0270822 | A1 | 11/2006 | Norsten |
| 2006/0289405 | A1 | 12/2006 | Oberste-Berghaus |
| 2009/0075176 | A1 | 3/2009 | Singh et al. |
| 2009/0104523 | A1 | 4/2009 | Mullin et al. |
| 2011/0033755 | A1 | 2/2011 | Eitouni et al. |

FOREIGN PATENT DOCUMENTS

| | | |
|---|---|---|
| JP | 2006-036925 | 2/2006 |
| WO | 88 03154 | 5/1988 |
| WO | 88/03154 | 5/1988 |
| WO | 98/16960 | 4/1998 |
| WO | 2007/113236 | 10/2007 |
| WO | 2007/142731 | 12/2007 |
| WO | 2010/039606 | 4/2010 |

OTHER PUBLICATIONS

WO patent application No. PCT/US2009/058371, International Search Report and Written Opinion mailed Apr. 30, 2010.

U.S. Appl. No. 12/286,898, Office Action mailed Jul. 20, 2011.

"Characteristics of new-type solid polymer electrolyte controlling nano-structure", Takeshi Niitani et al., Journal of Power Sources, Aug. 1, 2005, pp. 386-390.

International Search Report and Written Opinion for PCT/US2007/08435, mailed Jul. 28, 2008.

Takeshi Niitani, Mikiya Shimada, Kiyoshi Kawamura, Kiyoshi Kanamura, "Characteristics of new-type solid polymer electrolyte controlling nano-structure", Journal of Power Sources 146 (2005) 386-390.

Thomas H. Epps, III, Travis S. Bailey, Hoaid D. Pham, and Frank S. Bates, "Phase Behavior of Lithium Perchlorate-Doped Poly(styrene-b-isoprene-b-ethylene oxide) Triblock Copolymers," Chem. Mater. 2002, 14, 1706-1714.

Philip P. Soo, Biying Huang, Young-Il Jong, Yet-Ming Chiang, Donald R. Sadoway and Anne M. Mayes, Rubbery Block Copolymer Electrolytes for Solid-State Rechargeable Lithium Batteries, Journal of the Electrochemical Society, 146 (1) 32-37 (1999).

Mohit Singh, Lola Odusanya, Nitash Balsara, Abstract "Performance of Nanostructured Polymer Electrolytes in Li Batteries," presented at Mar. 2006 APS meeting, Mar. 14, 2006.

Mohit Singh, Lola Odusanya, Nitash Balsara, "Nanostructured polymer electrolytes: Decoupling ion conduction and mechanical properties," presented Sep. 13, 2006 (abstract available online Jul. 17, 2006), ACS Meeting, San Francisco.

Lola Odusanya, Mohit Singh, Nitash Balsara, "Synthesis and Characterization of Nanostructured Polymer Electrolytes," Poster at BATT Review Meeting, Lawrence Berkeley National Laboratory, Jun. 1, 2005.

Nitash Balsara, Mohit Singh, Lola Odusanya, "Nanostructured Polymer Electrolytes with High Conductivity and Elastic Modulus for Li ion Batteries," presented at 207th ECS Meeting, Quebec, May 15, 2005.

Mohit Singh, et al., "Effect of Molecular Weight on the Mechanical and Electrical Properties of Block Copolymer Electrolytes," Macromolecules 2007, 40 4578-4585.

Hany Eitouni, et al., "Opportunities and Challenges in Polymer Nanoscience," presented at Oak Ridge National Laboratory, May 23, 2005.

Ishrat M. Khan, Daryle Fish, Yadollah Delaviz, Johannes Smid, "ABA Triblock comb copolymers with oligo (oxyethylene) side chains as matrix for ion transport," Makromol. Chem. 190, 1069-1078 (1989).

P. Lobitz, A. Reiche and H. Fullbier, "Block copolymers of poly(ethyleneoxide) materials for polymer electrolytes (transport properties)," Journal of Power Sources, 43-44 (1993) 467-472.

U.S. Appl. No. 12/271,829, filed Nov. 14, 2008, Singh et al.

U.S. Appl. No. 61/195,012, "High elastic modulus polymer electrolytes suitable for preventing thermal runaway in lithium batteries", Mullin et al., filed Oct. 1, 2008.

U.S. Appl. No. 12/271,829, Office Action mailed Sep. 15, 2011.

Wang, Congxiao et al., "All solid-state lithium-polymer battery using a self-crosslinking polymer electrolyte", Journal of the Electrochemical Society, 150 (9) A1166-A1170, 2003.

U.S. Appl. No. 12/271,829, Office Action mailed Jan. 25, 2012.

U.S. Appl. No. 12/271,829, Office Action mailed Apr. 11, 2012.

U.S. Notice of Allowance mailed Aug. 15, 2012, issued in U.S. Appl. No. 12/271,829.

U.S. Office Action mailed Jul. 27, 2012, issued in U.S. Appl. No. 12/286,898.

Quirk et al. "Butyllithium-Initiated Anionic Synthesis of Well-Defined Polystyrene-block-ethylene oxide) Block Copolymers with Potassium and Salt Additives," Polymer International (1996), 36(1), 3-10 (2 Pages).

207ECS Meeting Program Information: AA1-Nanostructured and Functionalized Conducting Polymer Films and Related Materials, 2005 Technical Program, May 15-20, 2005 (6 Pages).

U.S. Appl. No. 13/664,345, filed Oct. 30, 2012, Mullin et al.

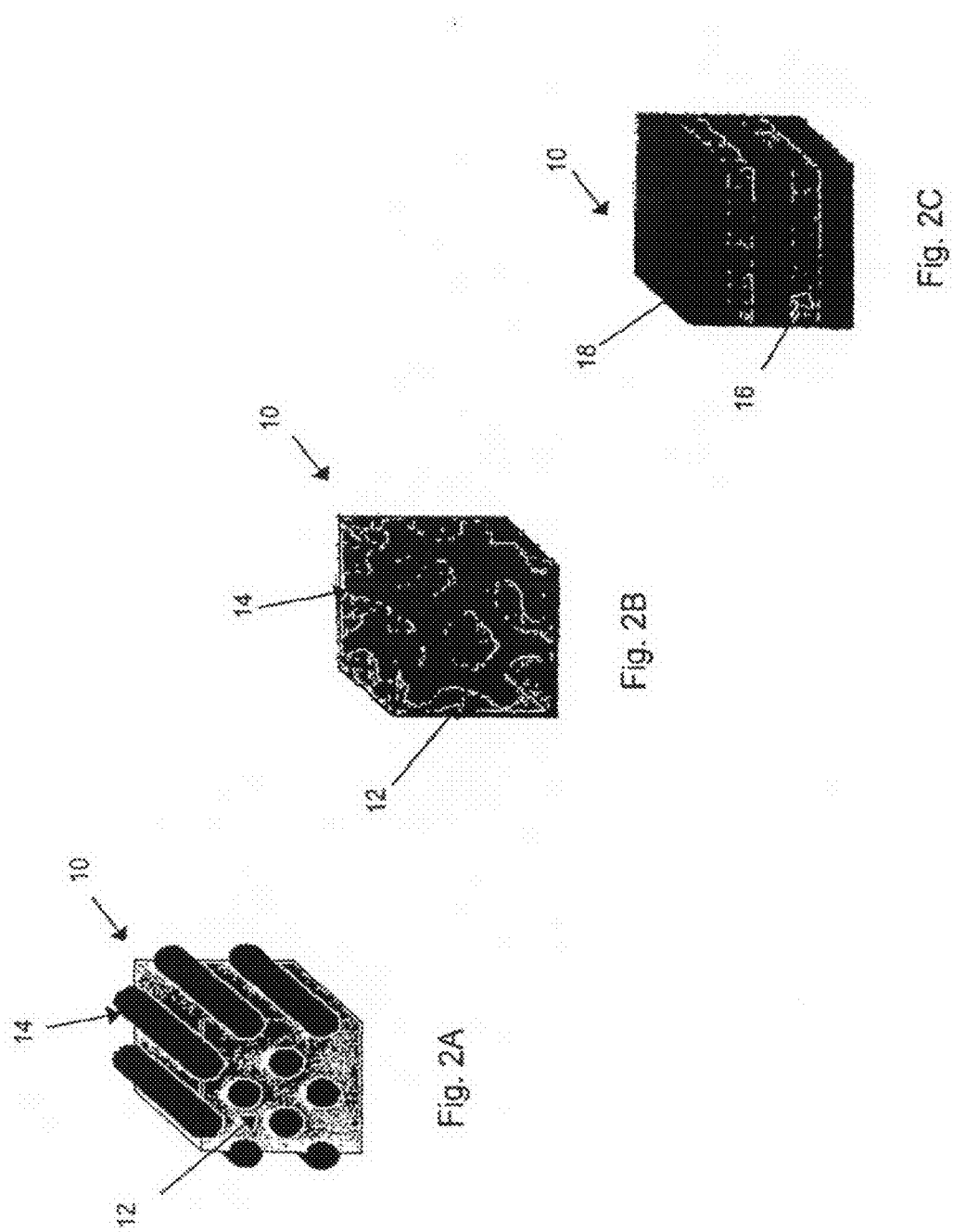

HIGH ELASTIC MODULUS POLYMER ELECTROLYTES

CROSS-REFERENCE TO RELATED APPLICATIONS

This application is a US National Stage entry under 35 U.S.C. 371 of the International Patent Application No. PCT/US07/08435 filed on Apr. 3, 2007, which claims priority to U.S. Provisional Patent Application No. 60/744,243 filed Apr. 4, 2006, titled HIGH ELASTIC MODULUS POLYMER ELECTROLYTES; and U.S. Provisional Patent Application No. 60/820,331 filed Jul. 25, 2006, titled SYNTHESIS OF DRY POLYMER ELECTROLYTES; the disclosures of which are incorporated herein by reference in their entirety and for all purposes.

STATEMENT OF GOVERNMENTAL SUPPORT

This invention was made with government support under Contract DE-AC02-05CH11231 awarded by the United States Department of Energy to The Regents of the University of California for the management and operation of the Lawrence Berkeley National Laboratory. The government has certain rights in this invention.

FIELD OF THE INVENTION

The invention relates to polymer electrolytes. More particularly, the invention relates to high elastic modulus, high ionic conductivity polymer electrolytes comprising linear block copolymers, and methods of making them.

BACKGROUND OF THE INVENTION

Polymer membranes with high ionic conductivity are important for applications such as solid-state batteries and fuel cells. The performance of these materials depends not only on their electrical properties but also on other properties such as shear modulus, permeability, and the like. The mechanical properties of polymer electrolytes are particularly important in secondary solid-state lithium (Li) batteries. One of the challenges in the field of rechargeable Li ion batteries is to combine high energy density with good cyclability and electrode stability. Batteries that employ Li metal anodes for high energy density applications suffer from failures due to side reactions and dendrite growth on the Li electrodes. Repeated cycling of the batteries causes roughening of the Li surface and eventually to dendrite formation, which reduces battery life and compromises safety.

Recent theoretical work indicates that dendrite growth can be stopped if the shear modulus of current polymer electrolytes can be increased by three orders of magnitude without a significant decrease in ionic conductivity. Other studies have shown that cation transport is intimately coupled to segmental motion of the polymer chains. These studies indicate that dendrite growth on the electrode surface can be prevented by introducing a highly rigid electrolyte (elastic modulus of about 1 GPa) between the two electrodes. This high modulus requirement essentially renders most rubbery polymer electrolytes incompatible with the electrode material, as the elastic moduli of typical rubbery polymers are about 1 MPa. For example, poly(ethylene oxide) (PEO) melt, one of the most studied polymer electrolytes, has an elastic modulus of less than 1 MPa. High ionic conductivity is obtained in soft polymers such as PEO because rapid segmental motion needed for ion transport also decreases the rigidity of the polymer. Glassy polymers such as polystyrene offer very high moduli (about 3 GPa) but are poor ion conductors. Thus, conductivity and high modulus have appeared to be almost mutually exclusive goals in polymer electrolytes.

There is, therefore, a need to develop a new methodology for decoupling the electrical and mechanical properties of polymer electrolyte materials. Such a material would be useful as a solid phase electrolyte for high energy density, high cycle life batteries that do not suffer from failures due to side reactions and dendrite growth on the Li electrodes.

SUMMARY OF THE INVENTION

The present invention provides a polymer that combines high ionic conductivity with the structural properties required for Li electrode stability. The polymer is useful as a solid phase electrolyte for high energy density, high cycle life batteries that do not suffer from failures due to side reactions and dendrite growth on the Li electrodes, and other potential applications. The polymer electrolyte includes a linear block copolymer having a conductive linear polymer block with a molecular weight of at least 5000 Daltons, a structural linear polymer block with an elastic modulus in excess of $1 \times 10^7$ Pa and an ionic conductivity of at least $1 \times 10^{-5}$ Scm$^{-1}$. The electrolyte is made under dry conditions to achieve the noted characteristics.

In specific embodiments, the linear block copolymer is a diblock copolymer characterized by bicontinuous lamellar phases of the polymer block constituents, and the structural polymer block can form a continuous rigid framework through which the conductive polymer block forms continuous nanostructured ionically conductive channels.

In one aspect, the invention relates to a polymer electrolyte. The electrolyte includes a linear block copolymer having a conductive polymer block with a molecular weight of at least 5000 Daltons, a structural polymer block with an elastic modulus in excess of $1 \times 10^7$ Pa, and an ionic conductivity of at least $1 \times 10^{-5}$ Scm$^{-1}$.

In another aspect, the invention relates to a method of making a polymer electrolyte. The method involves, in an oxygen and moisture free environment, forming a linear block copolymer having a conductive polymer block with a molecular weight of at least 5000 Daltons and a structural polymer block with an elastic modulus of at least $1 \times 10^7$ Pa and incorporating a Li salt into the linear block copolymer such that the resulting polymer electrolyte has an ionic conductivity of at least $1 \times 10^{-5}$ Scm$^{-1}$.

In a further aspect, the invention relates to battery cells comprising a Li anode, a cathode and linear block copolymer electrolyte in accordance with the invention disposed between the anode and cathode. The cell can be cycled without detrimental dendrite growth on the anode.

These and other aspects and advantages of the present invention are described below.

BRIEF DESCRIPTION OF THE DRAWINGS

The accompanying drawings, which are incorporated into and constitute a part of this specification, illustrate one or more embodiments and, together with the detailed description, serve to explain principles and implementations of the invention.

In the drawings:

FIGS. 2A-C illustrate embodiments of a PS-b-PEO diblock.

DETAILED DESCRIPTION OF SPECIFIC EMBODIMENTS

Figure 1A:
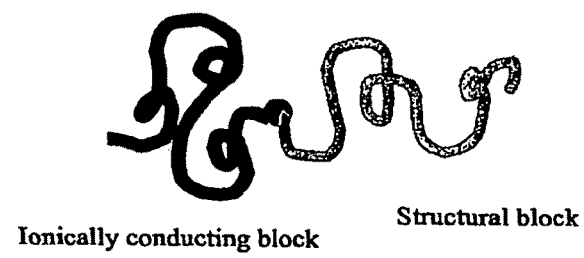
FIG. 1A is an illustration of a block copolymer in accordance with the present invention in isolation, showing the linearity of the polymer block chains.

Reference will now be made in detail to specific embodiments of the invention. Examples of the specific embodiments are illustrated in the accompanying drawings. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order to not unnecessarily obscure the present invention.

It will, of course, be appreciated that in the development of any actual implementation of the invention, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Introduction

As noted above, the present invention provides a polymer that combines high ionic conductivity with the structural properties required for Li electrode stability. The polymer is useful as a solid phase electrolyte for high energy density, high cycle life batteries that do not suffer from failures due to side reactions and dendrite growth on the Li electrodes, and other potential applications. The polymer electrolyte includes a linear block copolymer having a conductive linear polymer block with a molecular weight of at least 5000 Daltons, a structural linear polymer block with an elastic modulus in excess of $1 \times 10^7$ Pa and an ionic conductivity of at least $1 \times 10^{-5}$ Scm$^{-1}$. The electrolyte is made under dry conditions to achieve the noted characteristics.

In specific embodiments, the linear block copolymer is a diblock copolymer characterized by bicontinuous lamellar phases of the polymer block constituents, and the structural polymer block can form a rigid framework in which the conductive polymer block forms nanostructured ionically conductive channels.

Linear Block Copolymers

A linear block copolymer can be used to produce a polymer electrolyte that can combine high ionic conductivity with the structural properties required for Li metal electrode stability. The electrolyte is useful as a solid phase electrolyte for high energy density, high cycle life batteries that do not suffer from failures due to side reactions and dendrite growth on the Li electrodes. The linear block copolymer may be a composite polymer electrolyte having relatively soft (e.g., having an elastic modulus on the order of 1 MPa or less) nanoscale conducting channels embedded in a relatively hard (e.g., having an elastic modulus on the order of $1 \times 10^7$ Pa or more) polymer matrix that need not be ionically conductive. Ionic conductivity in the channels is conferred by a Li salt incorporated with the soft polymer block. It has been found that particular configurations and fabrications of such linear block copolymers enable the combination of high ionic conductivity and high elastic modulus in a polymer electrolyte.

While prior work in the field has suggested block copolymers as suitable materials for electrolytes, these prior block copolymers were composed of relatively soft (non-glassy) polymer blocks that were modified with various side chains.

The electrolytes of the present invention, however, comprise block copolymers with linear polymer block constituents, one of which is soft and conductive to Li ions; another of which is hard and need not be ionically conductive. FIG. 1A provides an illustration of such a copolymer in isolation, showing the linearity of the polymer block chains. The inventive polymer electrolytes include a linear block copolymer having a conductive linear polymer block with a molecular weight of at least 5000 Daltons, a structural linear polymer block with an elastic modulus in excess of $1 \times 10^7$ Pa and an ionic conductivity of at least $1 \times 10^{-5}$ Scm$^{-1}$.

Figure 1B:
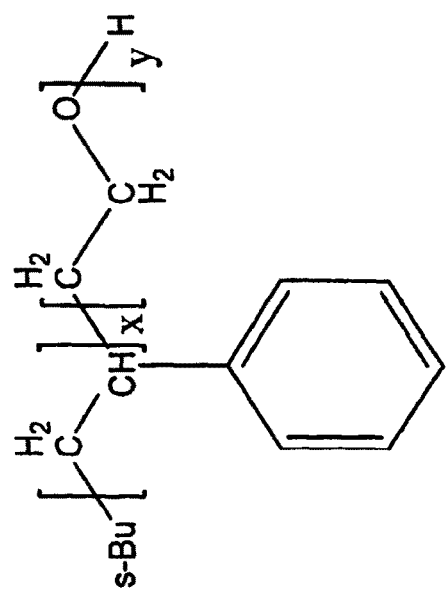
FIG. 1B depicts the chemical structure of a polystyrene-b-poly(ethylene oxide) (PS-b-PEO) diblock in accordance with one embodiment of the present invention.

In a specific embodiment, the copolymer is a linear diblock copolymer of poly(ethylene oxide) (a rubbery, linear polymer, highly ionically conductive when embedded with an appropriate Li salt) with polystyrene (a non-conductive, glassy, linear polymer); a polystyrene-b-poly(ethylene oxide) (PS-b-PEO) diblock, the chemical structure of which, is illustrated in FIG. 1B. This combination has been found to provide both the high ionic conductivity and high rigidity sought after for high performance solid state polymer electrolytes.

FIGS. 2A-C illustrate embodiments of a PS-b-PEO diblock in accordance with the invention. The PS-b-PEO diblock, generally numbered 10, exhibits an extensive phase behavior, which allows for bicontinuous phases. In these embodiments, in the bicontinuous PS-b-PEO phases, the major (e.g., greater than 50%) phase (PS) 12 provides a rigid framework for the nanostructured ionically conducting channels (PEO) 14.

FIGS. 2A-C illustrate the shape and placement of polymer blocks comprising conceptual diblocks in accordance with the present invention, and are not meant to be limiting. It will be known and understood that the diblock may be in any shape that is necessary and the placement of the polymers within the diblock may vary as needed. As illustrated in the FIG. 2A, the PEO channels 14 may be positioned in an orderly placement within the PS matrix 12. Alternatively, as illustrated in FIG. 2B, the PEO channels 14 may be branched, such as in a gyroid phase, within the PS matrix 12. FIG. 2C illustrates another specific embodiment in which the PEO channels 18 are layered in a lamellar arrangement with the PS matrix 16. While it has previously been believed that network morphologies are essential for ion transport, it was surprisingly found that diblock copolymers in accordance with the present invention with such non-network lamellar morphologies are very effective ion transporters.

In many instances, the diblock copolymer has a non-conducting phase that is continuous, and, in most cases, the major component, which differs from previously proposed block copolymer electrolytes. The mechanical properties of such block copolymer electrolytes are dominated by those of the non-conducting component. This enables independent control over the electrical and mechanical properties of the electrolyte. The structural linear polymer block major phase forms a rigid framework, with the conductive polymer block forming nanostructured ionically conductive channels through the rigid framework.

In specific embodiments, the linear block copolymer is a diblock copolymer and may be characterized by bicontinuous phases of the polymer block constituents such that there are continuous ionically-conductive channels (or pathways) through a continuous rigid framework. In this way, the beneficial properties of both polymer block materials (structural and conductive) exist throughout the material. Block copolymers are known in the art to self-assemble into a variety of structures or arrangements. As noted above, a particular arrangement for diblock copolymers in accordance with the present invention with advantageous properties is lamellar, although other arrangements are possible.

An important feature of the block copolymers is the combination of soft and hard polymer blocks to form a rigid material that is also highly ionically conductive. Thus, the structural polymer block has an elastic modulus of at least $1 \times 10^7$ Pa, and generally from about $1 \times 10^7$ Pa to 3 GPa. A suitable polymer for the structural block is polystyrene, a glassy polymer with an elastic modulus of about 3 GPa. Other mechanisms for obtaining suitable rigid frameworks include cross-linking and crystallization. The ionically conductive polymer, on the other hand, typically has an elastic modulus of no more than 1 MPa; poly(ethylene oxide), a specific material for which advantageous properties have been found in block polymers of the present invention, has an elastic modulus of less than 1 MPa.

Other examples of polymers suitable as conductive or structural polymers for these block copolymer electrolytes include poly vinyl pyrrolidine (conductive), poly acrylates (conductive), polyvinylcyclohexane (structural), epoxies (structural), and polypropylene (structural).

As noted above, the conductive polymer block chains of the block copolymer have a molecular weight of at least 5000 Daltons. This is notable since prior work in the field has indicated an inverse relationship between the molecular weight of conductive polymers and their ionic conductivity. To the contrary, it has been found that the ionic conductivity of the block copolymers of the present invention increases with increasing molecular weight of the constituent polymer blocks. Accordingly, in various embodiments, the structural polymer has a molecular weight of at least 5000 Daltons. Further, in various embodiments, the ionic conductivity of the block copolymer increases with increasing molecular weight of the conductive polymer block, so the conductive and structural polymer block chains each have molecular weights of at least 15,000 Daltons; or at least 50,000 Daltons; or up to about 100,000 Daltons or more. Ionic conductivity of greater than $1 \times 10^{-4}$ Scm$^{-1}$ and up to about $1 \times 10^{-3}$ Scm$^{-1}$ has been achieved with these relatively high molecular weight block copolymers in accordance with the present invention.

As noted above, ionic conductivity is achieved for the conductive polymer block by incorporating an appropriate Li salt into the conductive polymer block. It is important that incorporation of the Li salt be done in a controlled environment and under conditions selected to achieve the desired performance in the resulting polymer electrolyte product. This is discussed further below. Suitable Li salts include Li pentafluoromethane sulfonyl methide, lithium bis[1,2-oxalato(2-)-O,O']borate (LiBOB), and Li bis(trifluoro methane sulfonyl)methane, and others known in the art. One specific salt is LiN[SO$_2$CF$_3$]$_2$ (also known as LiTFSI). Self-assembly of the conductive polymer block results in ionically conductive channels in the ridged structural polymer block framework.

Further, as also described below, it has been found that the enhanced ionic conductivity obtained with increasing molecular weight of the conductive polymer block is correlated with a concentration of Li salt in a central portion of the ionically conductive channels in the block copolymer electrolytes.

While many specific embodiments of the invention exhibit a diblock copolymer structure, other structures are also possible. For example, an additional polymer block may be added to adjust the properties of the resulting copolymer, in this case a triblock copolymer. One suitable triblock copolymer is a polystyrene-block-polyisoprene-block poly(ethylene oxide) (S-I-EO) triblock copolymer. For example, a S-I-EO triblock copolymer with molecular weights of 11,000 Daltons for the polystyrene block, 6000 Daltons for the polyisoprene block, and 9000 Daltons for the poly(ethylene oxide) block was found to have a measured conductivity range from $4 \times 10^{-4}$ Scm$^{-1}$ to $9 \times 10^{-4}$ Scm$^{-1}$ in the 90-120° C. temperature range, for a molar ratio of Li ions to ethylene oxide, r=0.02.

Electrolyte Fabrication

Generally, a method of making a polymer electrolyte in accordance with the present invention comprises, in an oxygen and moisture free environment, forming a linear block copolymer having a Li ion conductive linear polymer block with a molecular weight of at least 5000 Daltons and a structural linear polymer block with an elastic modulus of at least $1 \times 10^7$ Pa; and incorporating a Li salt into the linear block copolymer, such that the resulting polymer electrolyte has an ionic conductivity of at least $1 \times 10^{-5}$ Scm$^{-1}$. Care must be taken in the manufacture of the linear block copolymer electrolytes to prevent adverse reaction of the Li salt and to obtain the polymer product with the advantageous performance noted herein.

A block copolymer electrolyte in accordance with the present invention can be made by synthesizing the structural polymer block by living anionic polymerization. Then, a monomer of the conductive polymer block and a cryptand catalyst are added to the structural polymer block living anionic polymerization mixture. The polymerization of the conductive block is then allowed to proceed. The reaction may proceed to completion and, after it is terminated with a suitable reagent, the resulting diblock copolymer product is precipitated and freeze-dried. Other living polymerization methods like cationic and radical polymerization techniques can also be used to synthesize the block copolymers.

To render the copolymer conductive to Li ions, a Li salt is blended with the freeze-dried diblock copolymer using a moisture-free solvent such that the Li salt is dissolved with the conductive polymer block. The resulting polymer/salt solution is then freeze dried to remove the solvent. The freeze-dried dry polymer/salt mixture can then be subjected to heat and pressure (compression molded) to form a free-standing polymer electrolyte film.

A detailed description of a method of making a linear diblock copolymer as applied to a specific embodiment follows. The following example will be described using SEO; however, it will now be realized that other materials and preparation methods may be used. As such, the following example is discussed for exemplary purposes only and is not intended to be limiting.

Synthesis of PS-b-PEO

In an exemplary embodiment of the invention, the diblock copolymer, polystyrene-b-poly(ethylene oxide) (SEO) is synthesized using living anionic polymerization to attain good control of the molecular weight and achieve low polydispersity. All of the synthetic steps are performed on a high-vacuum line and inside an argon glove box to ensure an oxygen and moisture free environment.

The first step is to purify the solvent, benzene, over calcium hydride for at least 12 hours at room temperature. Benzene is then distilled onto a sec-butyllithium stage for further purification.

The next step is purification of the styrene monomer, and synthesis of polystyrene. The styrene monomer is purified on calcium hydride ($CaH_2$) by stirring for a few hours to remove trace amounts of water. The monomer is then distilled into a flask (e.g., short-neck round-bottom flask) containing dibutyl magnesium (DBM). The monomer is stirred over DBM overnight. A clean reactor, in which polymerization will take place, is placed on the high-vacuum line and flamed with a torch to remove adsorbed water and solvent. After flaming, about 20 mL of the purified solvent is distilled from the sec-butyllithium stage into the clean reactor. This is done to prevent freezing and degassing a large amount of solvent. After the addition of 20 mL of benzene, the reactor is taken off the vacuum line, and into the glove box at which point the calculated amount of sec-butyllithium initiator required for reaction is pipetted into the reactor.

A very good seal is maintained during transfer back onto the vacuum line. After the reactor is placed back on the line, the mixture is frozen with liquid nitrogen and degassed 1, 2, 3, 4, or 5 times to remove trapped argon from the vessel and promote fast distillation. The remainder of the solvent can then be distilled into the reactor. In one arrangement, enough solvent is added to yield a mixture of approximately 8-10 wt % polymer in solution.

The first block, polystyrene (seen as 12 in FIGS. 2A-B, and 16 in FIG. 2C) is synthesized by distilling a calculated amount of styrene from the DBM stage into a graduated ampoule and then into the reacting vessel, which contains benzene and the sec-butyllithium initiator. The reaction is carried out at room temperature for approximately 12 hours and a characteristic yellow "living" polymer mixture is obtained upon completion. The mixture is stirred continuously during the reaction to ensure uniform mixing of the monomer. The reactor is then taken into the glove box and an aliquot is taken out and terminated with degassed methanol or isopropanol for characterization using gel permeation chromatography to determine its molecular weight.

This completes the synthesis of the first block, ready for the addition of the ethylene oxide (EO) block. A flask (e.g., short-neck round-bottom flask) with freshly powdered calcium hydride is placed on the vacuum line and opened up to vacuum to remove all air. The flask is maintained at 0° C. Ethylene oxide monomer, a gas at room temperature (b.p. 10° C.) is condensed onto the calcium hydride at 0° C. and left to stir overnight to remove residual moisture. The monomer-containing flask is maintained at a dry ice/IPA mixture temperature. The ethylene oxide is kept cold at all times during purification. The ethylene oxide/calcium hydride mixture is frozen and degassed twice before the purification steps.

The monomer is purified with two stages of n-butyllithium by stirring for 30 minutes at 0° C. at each stage. 10 mL of n-butyllithium in cyclohexane is used for each stage. The purifying agent, n-butyllithium, is completely dried by pulling vacuum to get rid of the cyclohexane solvent in which the n-butyllithium is dissolved. This can prevent contamination and ensures an accurate measurement of the amount of ethylene oxide (EO) monomer. The ethylene oxide monomer is distilled into a graduated ampoule maintained at 0° C. after purifying at both stages of n-butyllithium.

Following purification and distillation into a graduated ampoule, 1 ml of the EO monomer is distilled into the living polystyrene reactor for addition of a single EO unit. Only one EO unit is added to the living polystyrene chain because of the strong complexation of the lithium cation to the oxygen in the ethylene oxide unit. The Li cation shows a strong association with the ethylene oxide unit and, thus, no propagation reaction can occur. To polymerize the second block, a cryptand catalyst (e.g., tert-butyl phosphazene base ($tBu-P_4$)) is added to the reaction mixture (containing living EO capped polystyrene chains) to complex the lithium ions and facilitate the polymerization of ethylene oxide. To prepare the catalyst base, the solvent in which it is dissolved is removed and a known amount of benzene distilled into the flask. This solution can then be pipetted into the reactor in the glovebox. The reactor is then reattached to the high-vacuum line and degassed 1, 2, 3, 4, or 5 times to remove trapped argon from the vessel and promote fast distillation. The remainder of the EO is then distilled from the graduated ampoule into the reactor.

The reaction is allowed to proceed for three to four days at 45° C. during which the color changes to a dark blue. The diblock copolymer (SEO) is then terminated with methanol in the glove box and purified by precipitation in cold hexane. The precipitated polymer is dissolved in benzene and filtered through a 0.2 μm filter. The filtered polymer is then freeze dried to remove all solvent. The freeze-dried polymer is characterized by gel permeation chromatography (GPC) to determine the molecular weight and by nuclear magnetic resonance (NMR) to calculate the volume fraction of each block.

Electrolyte Preparation

Polymer electrolytes are prepared by blending the freeze-dried SEO copolymers with the lithium salt, $LiN[SO_2CF_3]_2$ (LiTFSI) in a moisture free environment. This is achieved in a few steps. A LiTFSI/THF solution (about 10% w/w) is prepared in the glove box, and stored as a stock solution. All the copolymer samples are weighed and vacuum dried in a heated antechamber and brought into the glove box. The dry copolymer samples are then dissolved in dry benzene. To this copolymer/benzene solution, the necessary amount of the LiTFSI stock solution is added in the argon glove box. All solvents used in the electrolyte preparation are doubly-distilled to remove trace amounts of moisture. The polymer/salt solution is then freeze-dried in a glove box compatible desiccator for one week to remove all solvent. The freeze-dried polymer/salt mixture is loosely packed into a pellet in a die that has a diameter slightly less than the spacer inner diameter. The pellet is placed in a Teflon™ bag along with a spacer, such that the pellet is in the center of the spacer's slot. The spacer is made of a non-conducting reinforced resin, and can withstand high pressure and temperature without deforming. The pellet is then subjected to a high pressure (about 1 kpsi) at about 100° C. This yields a clear, freestanding polymer electrolyte film with the spacer around it. The spacer defines the edge and the thickness (and hence the area, and the volume) of the freestanding polymer electrolyte film, and provides a means for easy transfer in and out of the membrane-electrode assembly. All the steps are carried out in the glove box.

Structure and Performance

While the invention is not limited by any particular theory, it is believed that the high elastic modulus, high ionic conductivity block copolymers of the present invention are correlated with a particular morphology. It has been found that for at least some specific embodiments of the invention with advantageous properties, the bicontinuous phases of the polymer block constituents of the diblock copolymer have a lamellar arrangement and that the Li salt segregates itself to the ionically conductive block channels. In addition, with increasing molecular weight of the polymer block constituents, the Li salt increasingly concentrates itself to a central portion of the ionically conductive block channels and ionic conductivity increases.

As described further below with reference to FIG. 8, the linear block copolymer electrolytes of the present invention exhibit good cycling performance. No dendrite formation was observed for 80 cycles in DC Li/polymer/Li test cells.

EXAMPLES

The following examples provide details relating to composition, fabrication and performance characteristics of block copolymer electrolytes in accordance with the present invention. It should be understood the following is representative only, and that the invention is not limited by the detail set forth in these examples.

To characterize the electrolyte, experimental data results were obtained by methods such as transmission electron microscopy (TEM), small angle X-ray scattering (SAXS), AC impedance spectroscopy, and rheology. AC impedance spectroscopy measurements were made using a test cell on thermo-stated pressed samples in the glove box, and a Solartron 1260 Frequency Response Analyzer machine connected to a Solartron 1296 Dielectric Interface. The polymer samples for TEM and SAXS were annealed using the same thermal history as that used for conductivity measurements. The electrolyte samples were kept at 120° C. for 2 hrs, and cooled to room temperature. Thin sections (about 50 nm) were prepared using an RMC Boeckeler PT XL Cryo-Ultramicrotome operating at −100° C. Imaging was done on a Zeiss LIBRA 200FE microscope operating at 200 kV. SAXS measurements were made on hermetically sealed samples. The data were collected for various temperatures between 140° C. and room temperature during cooling. Rheological measurements were performed using an ARES rheometer from Rheometric Scientific Inc. with a parallel plate geometry. Approximately 1 mm thick samples were placed between 8 mm plates for SEO, and 50 mm plates for PEO, in a closed oven with a Nitrogen ($N_2$) atmosphere. The ratio of Li ions to ethylene oxide moieties, r, in the electrolyte was varied from 0.02 to 0.10. Unless otherwise noted, due to the lack of qualitative changes in properties with salt concentration, data was obtained at r=0.02. Alternating current (AC) impedance and rheological data, obtained from mixtures of a 20 kg/mol PEO homopolymer and $Li[N(SO_2CF_3)_2]$, serve as the baseline for evaluating the properties of the composite electrolyte.

Table 1 lists the characteristics of the different kinds of copolymers that will be discussed:

TABLE 1

| Copolymer | Mn (PS) g/mol | Mn (PEO) g/mol | $\phi_{EO}$ | Morphology | d spacing (nm) |
| --- | --- | --- | --- | --- | --- |
| SEO(36-25) | 36400 | 24800 | 0.38 | Perforated Lamellae | 47.9 ± 0.8 |
| SEO(74-98) | 74000 | 98100 | 0.55 | Lamellar | 101.2 ± 3.4 |
| SEO(40-54) | 39700 | 53700 | 0.55 | Lamellar | 66.4 ± 1.4 |
| SEO(40-31) | 39700 | 31300 | 0.42 | Perforated Lamellae | 44.4 ± 0.6 |
| SEO(16-16) | 16200 | 16300 | 0.48 | Lamellar | 30.4 ± 0.3 |
| SIEO(11-6-9) | 11200 | 9000 | 0.31 | Lamellar | 33.0 ± 0.3 |

Two different block polymer types were utilized to obtain the experimental data. The first is polystyrene-block-poly (ethylene oxide) diblock copolymers (SEO) doped with lithium bis(trifluoromethylsulfonyl)imide, $Li[N(SO_2CF_3)_2]$. The PS-rich phase provides mechanical rigidity, while the PEO phase provides ionic conductivity. The second is a polystyrene-block-polyisoprene-block-poly(ethylene oxide) triblock copolymer (SIEO). The presence of the polyisoprene rubbery domains is known to increase the impact strength of polystyrene.

Figure 3:
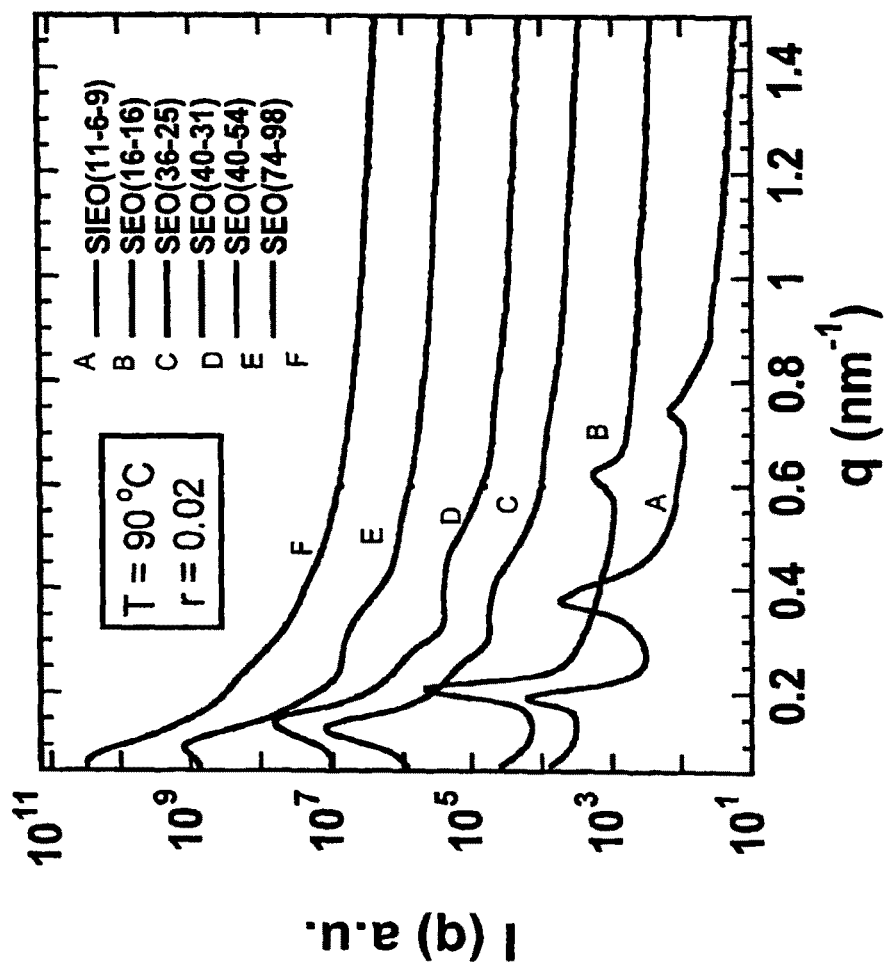
FIG. 3 is a graph illustrating SAXS profiles obtained from SEO/salt and SIEO/salt mixtures in accordance with the present invention.

FIG. 3 is a graph illustrating SAXS profiles obtained from SEO/salt and SIEO/salt mixtures. The SAXS data were obtained from SEO/salt and SIEO/salt mixtures with r=0.02 and at a temperature of 90° C. For clarification, SIEO (11-6-9) (marked A) has a ratio of polystyrene-polyisoprene-poly(ethylene oxide) of 11-6-9. SAXS data obtained from pure SEO and SIEO samples were indistinguishable from the data shown in FIG. 3. The long range order, as gauged by the sharpness of the primary and higher order peaks, is better in low molecular weight samples than in the high molecular weight samples. This is expected due to the slow diffusion in strongly segregated block copolymers.

The SAXS profiles of SEO (36-25) (marked C) are similar to perforated lamellar phases, while those from the other samples show the presence of a lamellar phase. TEM images of SEO (36-25) (not shown for brevity) indicate that the PEO lamellae appear dark and perforated, while the PS lamellae show no evidence of perforations, in agreement with the SAXS data shown in FIG. 3. Based on the similarity in the SAXS profiles obtained with and without salt, the addition of salt at low concentrations to the SEO copolymer may not affect the morphology. The TEM and SAXS data indicate the absence of an interpenetrating network phase in the block copolymer electrolytes.

Figure 4:
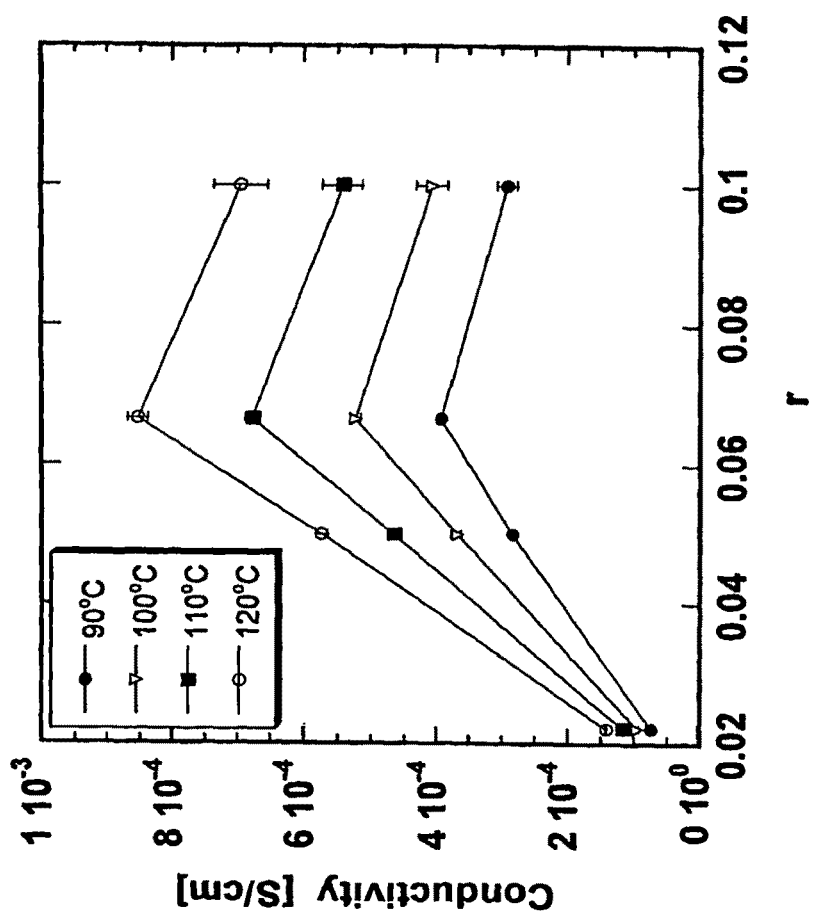
FIG. 4 is a graph illustrating the dependence of ionic conductivity on r (Li salt per EO unit) and temperature in SEO (36-25), a block copolymer electrolyte in accordance with the present invention.

FIG. 4 is a graph illustrating the dependence of ionic conductivity on r and temperature, respectively, in SEO (36-25). FIG. 4 illustrates that the conductivity has a maximum at r≈0.067, regardless of temperature. This trend is similar to that observed in PEO-salt homopolymer-based systems. At low salt concentrations, ionic conductivity increases with salt concentration due to the increase in the number of charge carriers. At high salt concentrations, transient cross linking of the polymer chains and neutral ion pairs result in reduced conductivity. FIG. 4 illustrates the conductivity at various temperature ranges. It illustrates that SEO (36-25) was conductive at 90° C. and higher.

Figure 5A:
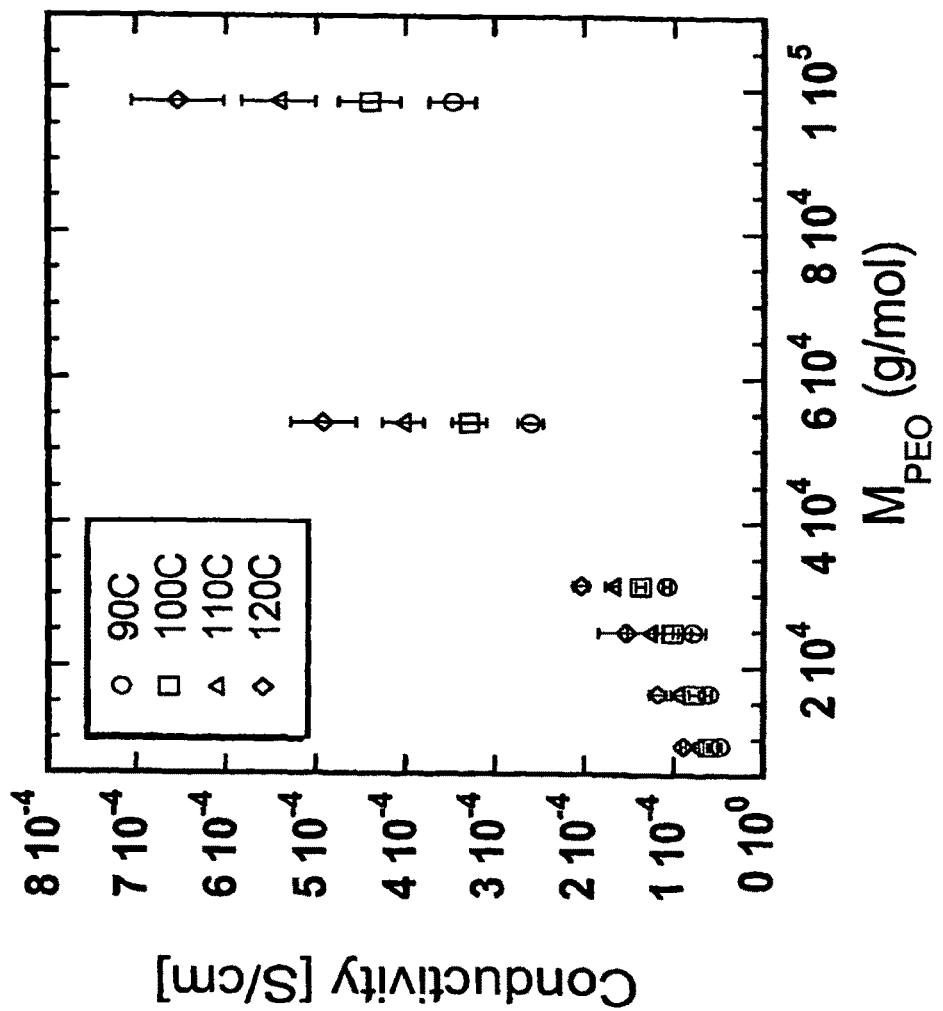
FIGS. 5A-5B are plots comparing ionic conductivity of block copolymer electrolytes in accordance with the present invention to the molecular weight of their respective PEO blocks.
Figure 5B:
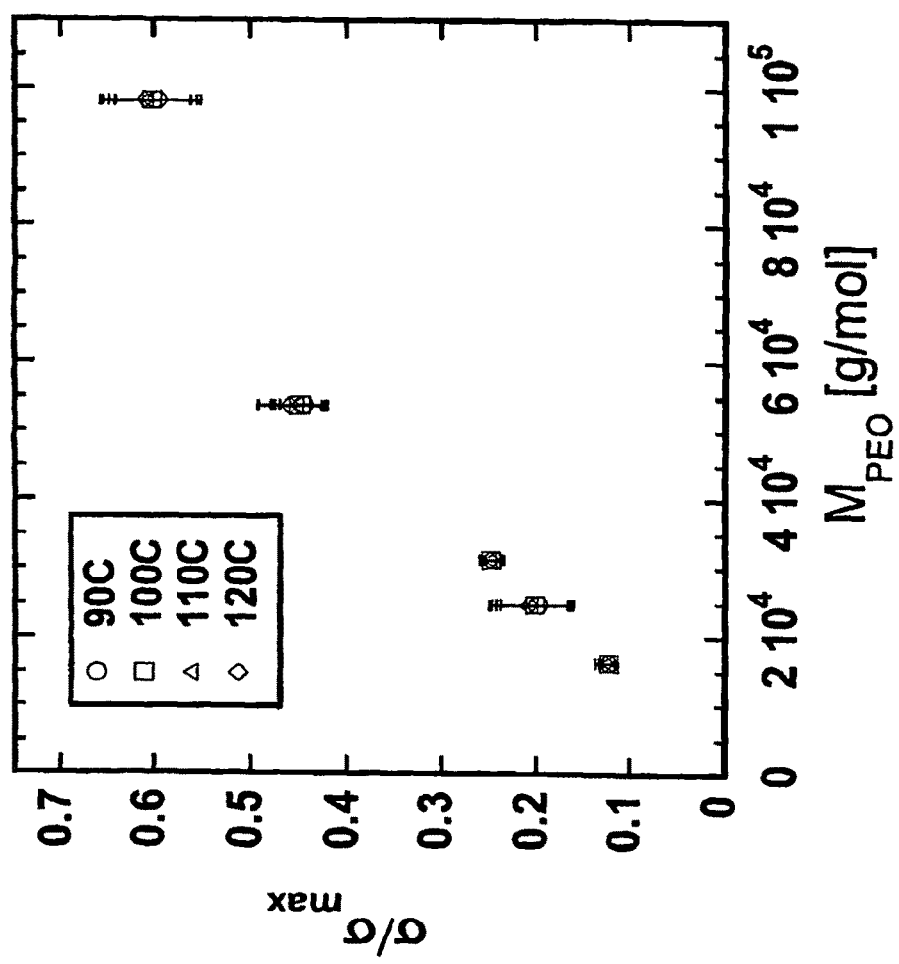

FIGS. 5A-5B are graphs comparing ionic conductivity of the composite electrolytes as a function of the molecular weights of the PEO blocks. FIG. 5A illustrates a systematic increase in conductivity with the molecular weight of the PEO block ($M_{PEO}$). The observed trend is opposite to that obtained in pure PEO/salt mixtures where the conductivity decreases with increasing molecular weight and eventually reaches a plateau. The conductivity, $\sigma_{PEO}$, of the PEO homopolymer with r=0.02 at 90° C. and 120° C. was measured to be $3.7 \times 10^{-4}$ S/cm and $5.6 \times 10^{-4}$ S/cm, respectively. The conductivity obtained in the highest molecular weight sample, SEO (74-98) (marked F in FIG. 3), is comparable to that of pure PEO. Data obtained (not shown) from SEO (74-98) at 100° C. show σ peaks at a value of about $10^{-3}$ S/cm at r=0.08. These values of conductivity are adequate for some battery applications.

The PEO volume fraction in the composite electrolyte, $\phi_{PEO}$, varied from 0.38 to 0.55. If all of the PEO channels in the nanostructured electrolyte provided conducting pathways for the ions, and if the conductivity of the PEO channels were identical to that of PEO homopolymers, then the value of the conductivity of a doped SEO sample, $\sigma_{max}$ would be the product of $\phi_{PEO}\sigma_{PEO}$. The ratio $\sigma/\sigma_{max}$ thus normalizes the measured conductivity data for differences in $\phi_{PEO}$. FIG. 5B is a plot of $\sigma/\sigma_{max}$ versus $M_{PEO}$. FIG. 5B shows that the ionic conductivity of the electrolytes may be mainly affected by $M_{PEO}$, and not by block copolymer composition.

FIGS. 5A and 5B illustrate that: (1) it is possible to make self-assembled conducting nanostructured electrolytes with non-conducting matrix phases, and (2) the magnitude of the conductivity of such electrolytes is in the range of the theoretical upper limit that can be expected from such systems. The samples were not subjected to any special processing steps to ensure that the PEO lamellae were connected or aligned. Connectivity of the PEO phase occurs reproducibly by quiescent annealing at 120° C. Although it has been widely understood that highly connected network phases are essential for high conductivity, the above data indicates that that is not the case.

FIG. 5B illustrates the fact that $\sigma/\sigma_{max}$ for the highest molecular weight sample is close to the theoretical maximum of 0.67 expected for a structure comprised of randomly oriented grains. It is believed that dissociated Li ions are tightly coordinated with the ether linkages in PEO, and thus disruption of this coordination could lead to faster ion transport. The disruption of coordination may be due to two reasons: (1) the contact between the ions and the polystyrene/poly(ethylene oxide) interfaces, and (2) the deformation of PEO chains due to self-assembly. The polystyrene/poly(ethylene oxide) interfacial area (per unit volume) decreases with increasing molecular weight. As noted above with reference to FIG. 3, potential reason (1) appears incorrect. As such, ion transport in microphases may be faster than in bulk.

In contrast, it is known that block copolymer chains stretch when they form ordered phases due to the traditional balance of energy and entropy. On average, PEO chains are stretched in the lamellae, compared to the homopolymer. The extent of stretching depends on copolymer chain length, N, and the Flory-Huggins interaction parameter between the blocks, $\chi$.

The range of the product $\chi_N$ in the SEO diblock copolymers ranged from 25 to 130 at 90° C., indicating that these copolymers in accordance with the invention are far from the weak segregation limit. Another indication of the stretched nature of the PEO chains is the scaling of the PEO lamellae thickness, $d_{PEO}$, calculated from the periodic length scale, d, given in Table 1 with $N_{EO}$, the number of EO units in PEO block. A least squares power law fit through the d versus N data yields $d_{PEO}=0.18*N_{EO}^{0.69}$ (both the prefactor and exponent were free parameters in the fit), which is the expected result in the strongly segregated limit. Thus, the stretched PEO chains in the high molecular weight block copolymers are not as tightly coordinated with Li ions compared to PEO random coils, which leads to enhanced conductivity.

Figure 6:
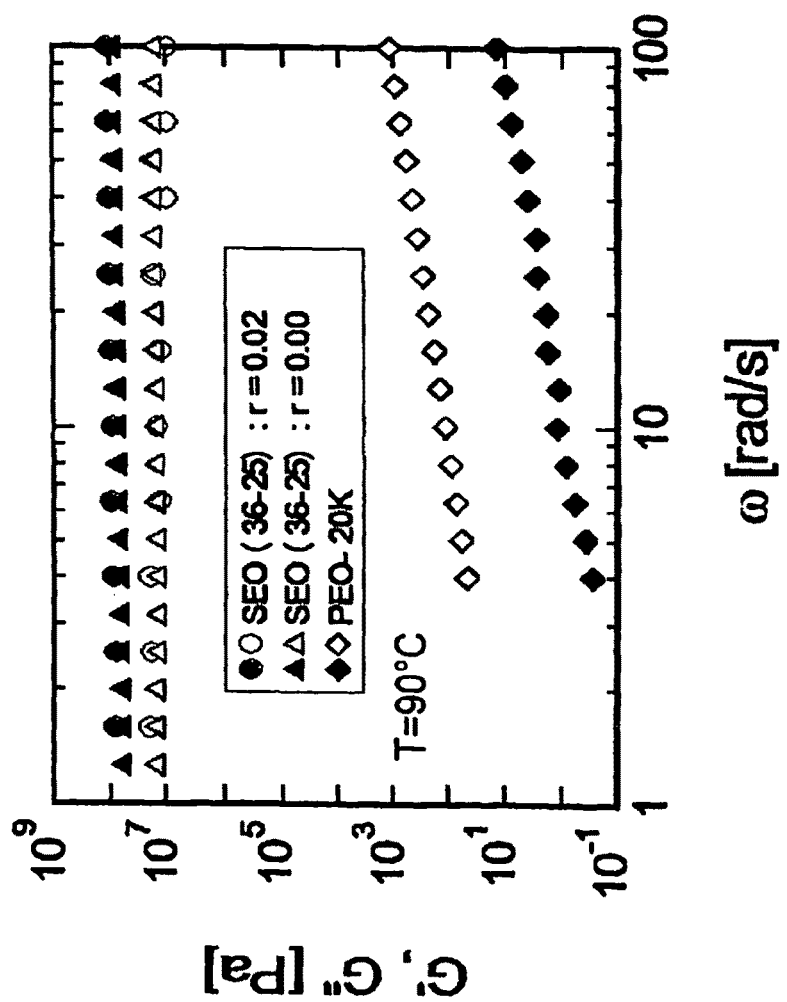
FIG. 6 is a graph illustrating the frequency dependence of the storage and loss shear moduli of SEO (36-25), a block copolymer electrolyte in accordance with the present invention, with and without salt and PEO.

FIG. 6 is a graph illustrating the frequency dependence of the storage and loss shear moduli. The graph shows the frequency (ω) dependence of the storage and loss shear moduli, G' and G", respectively, of pure SEO (36-25), SEO (36-25) with r=0.020, and pure PEO homopolymer. The data obtained from the pure SEO (36-25) and SEO (36-25) with r=0.020 are indistinguishable. The frequency-independence of the moduli and the fact that G' is an order of magnitude larger than G" indicate that the block copolymer electrolytes are elastic solids. The data also indicates that the addition of small amounts of salt has no detrimental effect on the mechanical properties of the materials. The value of G' obtained from the SEO (36-25) electrolyte is 100 times larger than the plateau modulus of pure PEO and 6 orders of magnitude larger than G' of the PEO homopolymer. The molecular weight of the PEO homopolymer is similar to that of the PEO block in the SEO (36-25) copolymer. Thus, nanostructured electrolytes have roughly half the conductivity of homopolymer PEO but larger shear moduli by several orders of magnitude.

Figure 7:
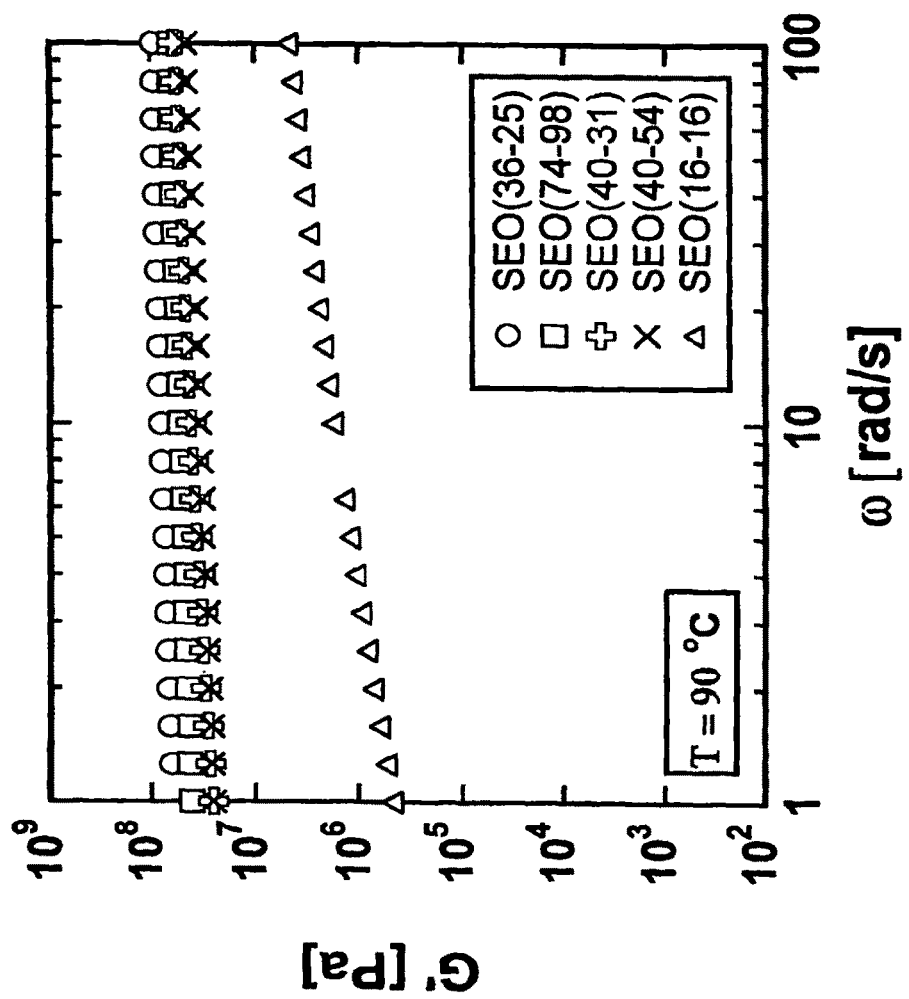
FIG. 7 is a graph illustrating the frequency dependence of elastic moduli for the series of copolymers referenced in FIG. 3.

FIG. 7 is a graph illustrating the frequency dependence of elastic moduli for the diblock copolymers referenced in FIG. 3. The higher molecular weight copolymers that exhibit high ionic conductivity yield elastic moduli of the order of $10^8$ Pa. By adding the PS block to the PEO chain, the shear modulus increases by several orders of magnitude while keeping the ionic conductivity near the level of pure PEO.

Figure 8:
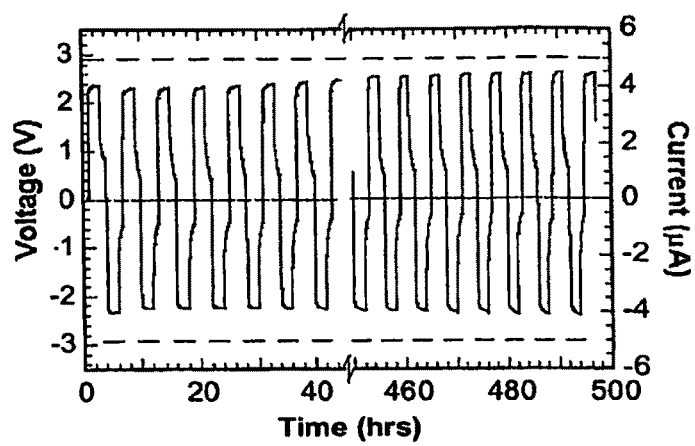
FIG. 8 is a plot of the results of DC cycling of a Li/SEO/Li cell with an electrolyte in accordance with the present invention.

FIG. 8 plots the results of cycling a Li/SEO (74-98) r=0.02/Li cell with a 250 μm thick electrolyte at 90° C. The cell was formed with a freestanding polymer electrolyte film formed as described above herein. A spacer with the freestanding polymer electrolyte film was then sandwiched between two aluminum masks that defined the exposed electrolyte area available for lithium (Li) deposition. This assembly was then secured to a slotted disk. The slots in the disk ensure that the electrolyte surface was exposed for Li deposition. The slotted-disk with 30 electrolyte/mask assemblies was then secured to a spindle in the Li deposition chamber. The spindle was connected to a motor that can rotate the spindle, along with the slotted plate with electrolyte/mask assemblies. Once the slotted plate was secured to the spindle, Li pellets were placed in the crucible of the vapor-deposition chamber. The deposition chamber was then closed and left overnight under a very high vacuum ($<10^{-3}$ mbar). The high vacuum ensures that the electrolyte and Li pellets are free of any adsorbed solvent molecules that may react with Li vapors. When the pressure in the deposition chamber was below $10^{-3}$ mbar, the crucible was heated to ~200° C., and Li was deposited from Li vapors onto the exposed surface of the electrolyte. The thickness of the deposited Li layer/film was monitored, and vapor deposition was stopped once a desired (~1 μm) Li-layer thickness was achieved. Then the deposition chamber was opened and the slotted plate was flipped and secured back to the spindle, exposing the other face of the freestanding electrolyte film that had not yet received any deposited Li. The deposition chamber was closed and the process of Li-deposition was repeated. This yields symmetric Li/SEO/Li cells for performing DC cycling measurements. In each cycle, a 50 µA/cm² current density was applied to the cell for 2 h, followed by a rest period of 1 h, followed by a 50 µA/cm² current density applied in the opposite direction. The voltage required to achieve this current density was independent of time over 80 cycles, indicating the lack of dendrite growth during these experiments.

The structure of the block copolymer electrolytes of the present invention was investigated to determine if a structural correlation for the observed properties could be determined. Poly(styrene-block-ethylene oxide) (SEO) copolymer electrolytes were prepared as described above. Samples were pressed at 120° C. into 0.1-1 mm thick disks using a mechanical press. All sample preparation was done without exposing the materials to atmospheric water or oxygen.

Electron microscopy images were analyzed to determine the width of the lithium and poly(ethylene oxide) channels. Micrographs were segmented into boxes that were approximately two times the periodicity of the structures. The minimum periodicity, $d_{min}$, was taken to be the true spacing of the nanostructured electrolyte. Regions which show a periodicity within 10% of $d_{min}$ were selected for further quantification. The intensity distribution of these images was normalized to maximize the dynamic range of contrast. A high-pass filter which removes low-frequency data below a radius of 30 pixels was used to remove some of the noise from the images. The image was thresholded, such that pixels are either black or white, to measure systematically the lamellae thicknesses. The channel thicknesses were measured by hand every 0.04 $d_{min}$ along the lamellae normal.

Figure 9:
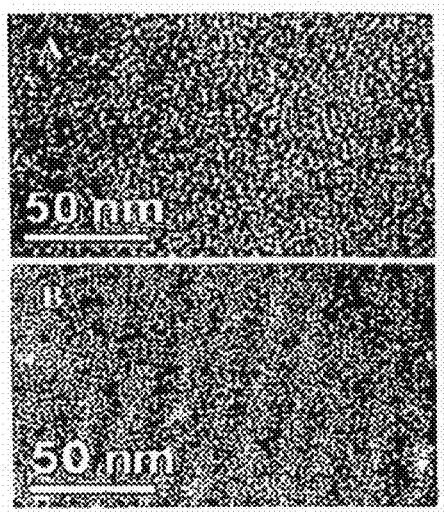
FIG. 9A is a bright field electron micrograph of a block copolymer in accordance with the present invention.
FIG. 9B is a lithium energy filtered electron micrograph of the same block copolymer region as FIG. 9A.

FIG. 9A is a bright field image of SEO (16-16)/salt mixture (r=0.085). The amorphous nature of the polymer is clearly visible. FIG. 9B is the lithium energy filtered micrograph of the same region as FIG. 9A. The light regions correspond to the presence of lithium, and the dark regions to the absence of lithium. Since the salt segregates itself to the PEO channels, the microstructure is now clearly visible and it is highly suggestive of a lamellar morphology.

Figure 10:
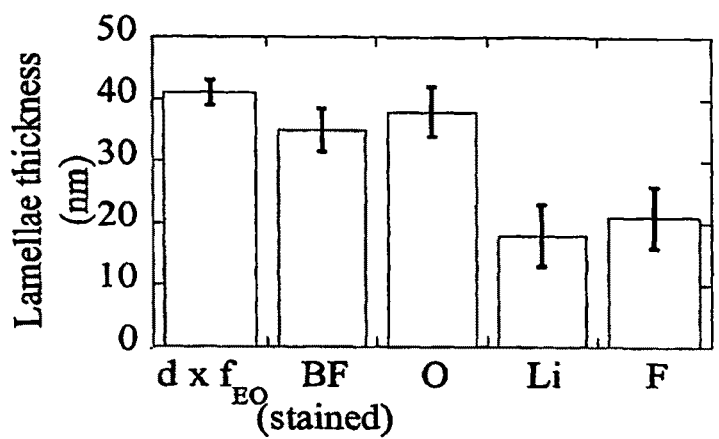
FIG. 10 presents data showing lamellae thicknesses for block copolymers in accordance with the present invention obtained from various measurements.
Figure 11:
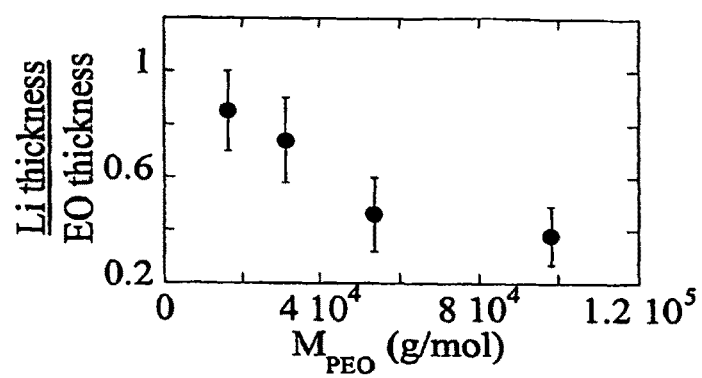
FIG. 11 is a plot of Li lamellae thickness normalized by the PEO lamellae thickness as a function of molecular weight.

Measurements of the thickness of the lithium salt and poly (ethylene oxide) lamellae are shown in FIG. 10 for SEO (74-98) at a salt concentration of r=0.085. The first column corresponds to the product of the periodicity observed in our images and the volume fraction of ethylene oxide in the copolymer. The second column is the thicknesses of PEO lamellae measured from bright field images of neat SEO copolymers stained with $RuO_4$. The last three columns correspond to lamellae measurements taken on energy filtered TEM images of O, Li and F. The first three columns are a measure of the PEO lamellae thickness, while the last two are a measure of the Li channels. It is clear from FIG. 10 that the salt lamellae are thinner than the PEO channels for SEO (74-98) at a salt concentration of r=0.085. The size of the Li domains were normalized by the ethylene oxide domains to determine the extent of this concentration effect as a function of the molecular weight of PEO, $M_{PEO}$, and these results are plotted in FIG. 11. It is clear that the thinning of the lithium lamellae is more dramatic for polymers with higher molecular weight.

Figure 12:
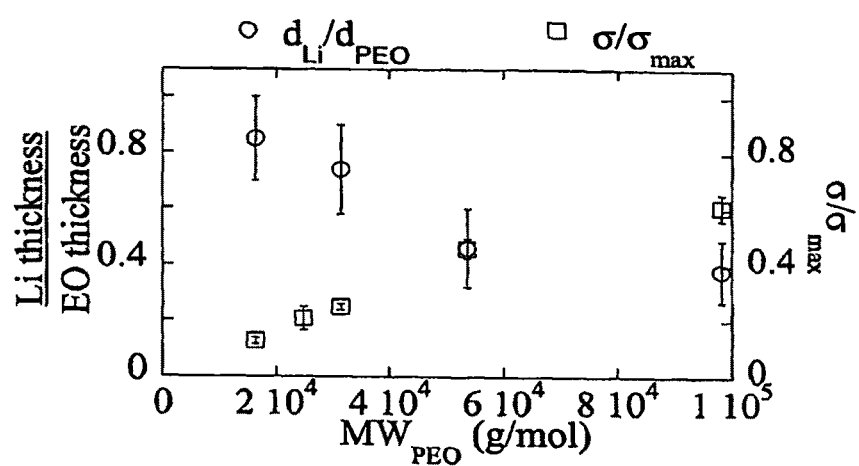
FIG. 12 is a plot comparing the normalized Li lamellae thickness and normalized conductivity versus molecular weight for various block copolymers in accordance with the present invention.

FIG. 12 is a comparison of the lithium salt distribution and the ionic conductivity of the copolymer electrolytes. There is a clear inverse relationship between the extent to which the Li segregates away from the interface and the ionic conductivity. It is concluded that by constructing SEO copolymer/salt mixtures where $M_{PEO}$ is high, a novel lithium salt structure within the nanostructured copolymer, with Li salt concentrated in a central portion of the ionically conductive polymer block, is produced, which results in highly conductive materials.

Nanostructured polymer electrolytes with soft conducting channels embedded in a hard insulating matrix are beneficial for applications that require independent control over mechanical and electrical properties. The data presented above indicate that network phases are not necessary to obtain ionic conductivity, which allows for the possibility of using a wide variety of morphologies for designing ionically conducting polymers. No special processing is needed to create percolating conducting pathways in these materials; they are formed entirely by quiescent self-assembly. This suppresses dendrite growth in Li-polymer batteries and provides a cost-effective solution for combining high energy density with good cyclability.

Applications

Figure 13:
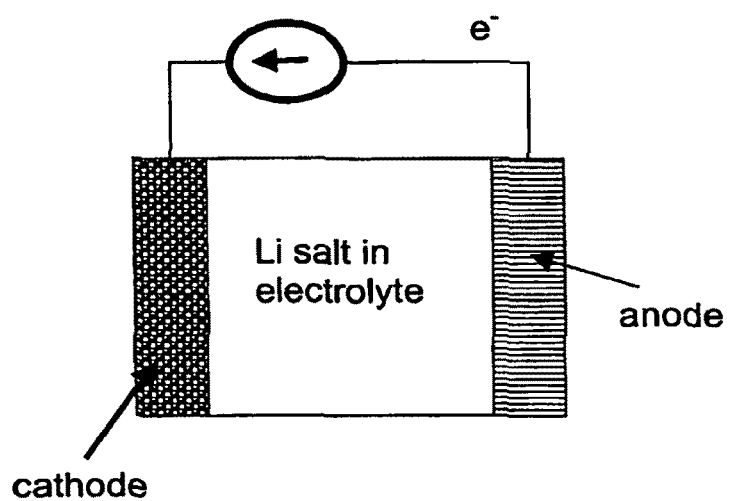
FIG. 13 is a simple schematic diagram of a battery cell in accordance with the present invention.

The electrolytes of the present invention are useful as solid phase electrolytes for high energy density, high cycle life batteries that do not suffer from failures due to side reactions and dendrite growth on the Li electrodes. In one aspect, the invention relates to a battery cell, a simple schematic diagram of which is provided in FIG. 13, comprising a lithium anode, a cathode, and a solid phase block copolymer electrolyte in accordance with the present invention disposed between the anode and cathode. The cell can be cycled without detrimental dendrite growth on the anode.

The invention may also be used, for example, as a power source for electronic media such as cell phones, media players (MP3, DVD, and the like), laptops and computer peripherals, digital cameras, camcorders, and the like. It may also be beneficial for applications in electric vehicles and hybrid electric vehicles.

CONCLUSION

Although the foregoing invention has been described in some detail for purposes of clarity of understanding, it will be apparent that certain changes and modifications may be practiced within the scope of the appended claims. It should be noted that there are many alternative ways of implementing both the process and compositions of the present invention. Accordingly, the present embodiments are to be considered as illustrative and not restrictive, and the invention is not to be limited to the details given herein, but may be modified within the scope and equivalents of the appended claims.

The invention claimed is:

1. A polymer electrolyte, comprising:
   a linear block copolymer having,
      a Li-ion conductive linear polymer block with a molecular weight of at least 5000 Daltons;
      a glassy structural linear polymer block comprising polystyrene with an elastic modulus in excess of $1 \times 10^7$ Pa;
      and an ionic conductivity of at least $1 \times 10^{-5}$ Scm$^{-1}$.

2. The electrolyte of claim 1, wherein the linear block copolymer is a diblock copolymer.

3. The electrolyte of claim 2, wherein the diblock copolymer is characterized by bicontinuous phases of the conductive polymer block and the structural polymer block.

4. The electrolyte of claim 3, wherein the structural linear polymer block comprises a major phase of the block copolymer.

5. The electrolyte of claim 4, wherein the major phase structural polymer block forms a rigid framework and the conductive polymer block forms nanostructured ionically conductive channels with the rigid framework.

6. The electrolyte of claim 1, wherein the structural polymer has a molecular weight of at least 5000 Daltons.

7. The electrolyte of claim 1, wherein the structural polymer has an elastic modulus of from about $1 \times 10^7$ Pa to 3 GPa.

8. The electrolyte of claim 1, wherein the conductive polymer has an elastic modulus of no more than 1 MPa.

9. The electrolyte of claim 3, wherein the conductive and structural polymers each have molecular weights of at least 15,000 Daltons.

10. The electrolyte of claim 3, wherein the conductive and structural polymers each have molecular weights of at least 50,000 Daltons.

11. The electrolyte of claim 1, wherein the structural polymer block is ionically non-conductive.

12. The electrolyte of claim 1, wherein the linear block copolymer is a polystyrene-block-poly(ethylene oxide) diblock copolymer.

13. The electrolyte of claim 1, wherein the conductive polymer block comprises poly(ethylene oxide).

14. The electrolyte of claim 1, wherein the conductive polymer block further comprises a Li salt.

15. The electrolyte of claim 14, wherein the Li salt is concentrated in a central portion of the ionically conductive channels.

16. The electrolyte of claim 1, wherein the ionic conductivity of the block copolymer increases with increasing molecular weight of the conductive polymer block.

17. The electrolyte of claim 1, wherein the ionic conductivity is at least $1 \times 10^{-4}$ Scm$^{-1}$.

18. The electrolyte of claim 3, wherein the bicontinuous phases have a lamellar arrangement.

19. The electrolyte of claim 1, wherein the block copolymer is a triblock copolymer further comprising an additional linear polymer block.

20. The electrolyte of claim 19, wherein the triblock copolymer is a polystyrene-block-polyisoprene-block poly(ethylene oxide) (S-I-EO) triblock copolymer.

21. A method of making a polymer electrolyte, comprising:
in an oxygen and moisture free environment,
forming a linear block copolymer having a Li-ion conductive linear polymer block with a molecular weight of at least 5000 Daltons and a glassy structural linear polymer block comprising polystyrene with an elastic modulus of at least $1 \times 10^7$ Pa; and
incorporating a Li salt into the linear block copolymer;
wherein the resulting polymer electrolyte has a ionic conductivity of at least $1 \times 10^{-5}$ Scm$^{-1}$.

22. The method of claim 21, wherein the linear block copolymer is a diblock copolymer.

23. The method of claim 22, wherein the method comprises:
synthesizing the structural polymer block by living anionic polymerization;
adding a monomer of the conductive polymer block and a cryptand catalyst to the structural polymer block living anionic polymerization mixture;
allowing a diblock copolymerization reaction to proceed;
terminating the reaction;
precipitating and freeze-drying the resulting diblock copolymer product;
blending the freeze-dried diblock copolymer with the Li salt in a dry solution such that the Li salt is dissolved into the conductive polymer block; and
freeze-drying the polymer/salt solution.

24. The method of claim 23, further comprising subjecting a portion of the freeze-dried polymer/salt solution to heat and pressure to form a freestanding polymer electrolyte film.

25. The method of claim 24, wherein the conductive polymer block comprises poly(ethylene oxide).

26. The method of claim 25, wherein the linear block copolymer is a polystyrene-block-poly(ethylene oxide) diblock copolymer.

27. The method of claim 26, wherein the Li salt is LiN[SO$_2$CF$_3$]$_2$.

28. A battery cell, comprising:
a Li anode;
a cathode; and
a solid phase polymer electrolyte disposed between the anode and cathode, the electrolyte, comprising:
a linear block copolymer having,
a Li-ion conductive linear polymer block with a molecular weight of at least 5000 Daltons;
a glassy structural linear polymer block comprising polystyrene with an elastic modulus in excess of $1 \times 10^7$ Pa; and
an ionic conductivity of at least $1 \times 10^{-5}$ Scm$^{-1}$.

29. The cell of claim 28, wherein the conductive polymer has an elastic modulus of no more than 1 MPa.

30. The cell of claim 29, wherein the conductive and structural polymers each have molecular weights of at least 15,000 Daltons.

31. The cell of claim 30, wherein the conductive and structural polymers each have molecular weights of at least 50,000 Daltons.

32. The cell of claim 31, wherein the conductive polymer block comprises poly(ethylene oxide).

33. The cell of claim 32, linear block copolymer is a polystyrene-block-poly(ethylene oxide) diblock copolymer.

34. The cell of claim 33, wherein the Li salt is LiN[SO$_2$CF$_3$]$_2$.

35. The cell of claim 28, wherein the cell can be cycled at least 80 times without dendrite growth on the anode.

36. The electrolyte of claim 19, wherein the additional linear block copolymer is the same as one of the conductive linear block copolymers or the structural linear block copolymers.

37. The electrolyte of claim 19, wherein the additional linear block copolymer is different from both the conductive linear block copolymers and the structural linear block copolymers.

* * * * *